United States Patent
Asotra et al.

(10) Patent No.: US 8,569,278 B2
(45) Date of Patent: Oct. 29, 2013

(54) ANTI-HISTAMINE COMPOSITIONS AND USE THEREOF

(75) Inventors: Satish Asotra, Brampton (CA); Jerzy Zadykowicz, Mississauga (CA); Kalpana Vanam, Albertson, NY (US); Shen Gao, Botton (CA)

(73) Assignee: Taro Pharmaceuticals North America, Inc., Grand Cayman (KY)

( * ) Notice: Subject to any disclaimer, the term of this patent is extended or adjusted under 35 U.S.C. 154(b) by 346 days.

(21) Appl. No.: 12/162,171

(22) PCT Filed: Jan. 25, 2007

(86) PCT No.: PCT/US2007/001875
§ 371 (c)(1),
(2), (4) Date: Jul. 25, 2008

(87) PCT Pub. No.: WO2007/087344
PCT Pub. Date: Aug. 2, 2007

(65) Prior Publication Data
US 2009/0048268 A1    Feb. 19, 2009

Related U.S. Application Data

(60) Provisional application No. 60/761,832, filed on Jan. 25, 2006.

(51) Int. Cl.
*A01N 43/00*    (2006.01)
*A61K 31/33*    (2006.01)

(52) U.S. Cl.
USPC ........... 514/183; 514/225.04

(58) Field of Classification Search
None
See application file for complete search history.

(56) References Cited

U.S. PATENT DOCUMENTS

| | | |
|---|---|---|
| 4,464,469 A | 8/1984 | Parr et al. |
| 6,071,523 A | 6/2000 | Mehta et al. |
| 6,102,254 A | 8/2000 | Ross |
| 6,171,618 B1 | 1/2001 | Johnson et al. |
| 6,399,079 B1 | 6/2002 | Mehta et al. |
| 6,436,374 B1 | 8/2002 | Kurz et al. |
| 6,790,847 B2 | 9/2004 | Walch |
| 2003/0045503 A1 | 3/2003 | Knigge |
| 2003/0129209 A1 | 7/2003 | Walch |
| 2005/0143471 A1* | 6/2005 | Gao et al. .............. 514/649 |
| 2005/0153946 A1 | 7/2005 | Hirsh et al. |
| 2005/0175642 A1 | 8/2005 | Asotra et al. |

FOREIGN PATENT DOCUMENTS

| | | |
|---|---|---|
| JP | 2002-516849 A | 6/2002 |
| JP | 2003-212773 A | 7/2003 |
| WO | WO-99/62498 A1 | 12/1999 |
| WO | WO-03/039485 | 5/2003 |
| WO | WO 03034991 A2 * | 5/2003 |
| WO | WO-2005/076829 A2 | 8/2005 |
| WO | WO-2007/087344 A2 | 8/2007 |

OTHER PUBLICATIONS

Jaber et al., (Determination of ceritizine dihydrochloride, related impurities and preservatives in oral solution and tablet dosage forms using HPLC, Journal of Pharmaceutical and Biochemical Analysis 36 (2004), pp. 341-350).*
Campoli-Richards et al "Cetirizine: A review of its pharmacological properties and clinical potential in allergic rhinitis, pollen-induced asthma, and chronic urticaria", vol. 40, Issue 5, Nov. 1990, Addis international.*
Coulie et al, Drug Development Research 14:199-206 (1989).*
Tanaka et al., "Uptake of histamine by mouse peritoneal macrophages and a macrophage cell line," RAW264.7, Am J Physiol Cell Physiol, Apr. 2003, vol. 285, pp. 592-598, p. 593, para. 4.
Form PCT/ISA/220 (Transmittal of International Search Report and Written Opinion).
Form PCT/ISA/210 (International Search Report).
Form PCT/ISA/237 (Written Opinion).
Handbook of Pharmaceutical Excipients, Third Ed., A.H. Kibbe (Ed.), Pharmaceutical Press, London, UK, 2000, pp. 442, 79, 53.
Merck Index, 12th Ed., No. 1878.
Pfizer, "Zyrtec® (cetirizine hydrochloride): Tablets, Chewable Tablets and Syrup," May 2006, http://www.pfizer.com/files/products/uspi_zyrtec.pdf.

* cited by examiner

*Primary Examiner* — Brandon Fetterolf
*Assistant Examiner* — Jean Cornet
(74) *Attorney, Agent, or Firm* — Venable LLP; Michael A. Gollin; Daniel A. Kopp

(57) ABSTRACT

The present invention provides for a storage stable pharmaceutical liquid solution for oral administration having a pharmaceutically effective amount of an antihistamine and having a purity equal to or greater than about 99% by weight-based HPLC assay, residual solvents of less than about 0.5%, and a total impurity of less than about 0.2%. The storage stable solution preferably contains cetirizine. The present invention further provides a process of preparing the storage stable pharmaceutical liquid solution as well as a method of treating a mammal with a therapeutically effective amount of cetirizine in the stable pharmaceutical liquid solution.

15 Claims, No Drawings

ANTI-HISTAMINE COMPOSITIONS AND USE THEREOF

BACKGROUND OF THE INVENTION

Cetirizine is a metabolite of the anti-histamine, hydroxyzine. Similar to other second-generation anti-$H_1$ receptor antagonists, cetirizine does not cross the blood brain barrier and is considered a peripherally active anti-histamine with few central nervous system effects. Studies have shown that cetirizine provides safe and effective, symptomatic relief of seasonal allergies. Advantages to using cetirizine as an antihistamine include minimal sedative effect, little anticholinergic activity and a longer acting duration.

Cetirizine is water soluble, and rapidly absorbed. Tablets and syrup formulations of cetirizine have been commercially manufactured and marketed. However, cetirizine pharmaceutical formulations are subject to degradation that occurs during manufacture and storage. U.S. Pat. No. 6,171,618 teaches that an esterfication process of the cetirizine occurs when low molecular weight esters or alcohols are present in a reactive mixture with cetirizine. In particular, high boiling point alcohols, especially glycerin, should not be present during the manufacturing and in formulations of cetirizine. The resultant ester impurities can cause the formulations to deviate from regulatory purity requirements and decrease the shelf-life of the formulations.

Spill resistant pharmaceutical formulations have been described in U.S. Pat. Nos. 6,102,254, 6,071,523 and 6,399,079. The spill resistant formulations have been described by the physical properties of (a) extrudability under light manual pressure from a squeezable container or a proxy (e.g. a syringe with a 5 mm orifice), and (b) spreadability in a spoon bowl measured by extruding the formulation into a spoon bowl and determining whether the material levels or spreads to the edges of the spoon bowl Spreadability also contributes to accuracy of measurement.

Surprisingly, we have discovered a spill resistant cetirizine formulation, containing high levels of low molecular weight polyhydric alcohol that does not form the most common cetirizine formulation degradative products, has a high degree of purity and increased storage time.

SUMMARY OF THE INVENTION

The invention is to a stabilized pharmaceutical liquid formulation comprising an antihistamine and having a purity equal to or greater than about 99% by weight-based HPLC assay, residual solvents of less than about 0.5%, and a total impurity of less than about 0.2%. Surprisingly, the impurities are often less than 0.1% of the active. The stability of the active ingredient during the shelf storage of the product allows for an extended shelf life of the product compared to other antihistamine formulations. Consequently, one embodiment of the invention allows for antihistamine solutions that have a storage stability of up to 24 months. Another embodiment would allow for a storage stability of up to 36 months.

One embodiment of the invention is directed to a stabilized liquid formulation of cetirizine, or a salt thereof. The particular formulations described herein will contain cetirizine, a carrier component and a thickener. In one embodiment the carrier may be glycerin and the thickener is a carbomer. The formulation may contain at least one organoleptic agent, and other pharmaceutically acceptable excipients may be present to provide a palatable, stable, and pleasing composition.

In addition to pharmaceutically acceptable excipients, the formulation may comprise other active pharmaceutical ingredients in combination with the antihistamine. Some embodiments of the inventive formulation may include a decongestant, an analgesic, an antitussive, an expectorant, or any combination of two or more thereof.

The storage stable solution of the present invention has a pH of between about 5.4 and 8.0, more preferably between 6.2 and 7.3.

Another embodiment of the invention is directed towards a method of treating a human in need of cetirizine by administering a therapeutically effective amount of the storage stable pharmaceutical liquid solution of the invention.

An additional embodiment of the invention is a method of preventing the formation of impurities in a pharmaceutical liquid formulation comprising mixing an antihistamine in a storage stabilizing vehicle.

Additionally, there is disclosed the method of providing an extended product shelf life, that method comprising mixing the antihistamine with a storage stable vehicle.

DETAILED DESCRIPTION

In describing embodiments of the present invention, specific terminology is employed for the sake of clarity. However, the invention is not intended to be limited to the specific terminology so selected. It is to be understood that each specific element includes all technical equivalents, which operate in a similar manner to accomplish a similar purpose. The above-described embodiments of the invention may be modified or varied, and elements added or omitted, without departing from the invention, as appreciated by those skilled, in the art in light of the above teachings. Each reference cited herein is incorporated by reference as if each were individually incorporated by reference.

The inventive solution has, as the active pharmaceutical agent, an antihistamine, evenly dissolved in a semi-solid aqueous vehicle. A preferred antihistamine is cetirizine. Cetirizine, a piperazine derivative and carboxylated metabolite of hydroxyzine, is a potent histamine $H_1$-receptor antagonist with antiallergic properties. Cetirizine is used herein to describe not only the free compound of cetirizine, but also any pharmaceutically acceptable salt thereof. Preferred are the acid addition salts, in particular, cetirizine dihydrochloride. The term cetirizine also includes racemic mixtures and the enantiomers of cetirizine.

The solution provides a method of treating allergic conditions, such as allergic rhinitis and chronic uticaria in mammals. The methods include administering to a subject suffering from an allergic condition a storage stable pharmaceutical composition according to the invention. In one embodiment, the subject is a human. In another embodiment the allergic condition is allergic rhinitis or chronic idiopathic utircaria. The storage stable pharmaceutical composition can be administered to a patient in a dosage range of, for example, 0.5 mg to about 15 mg per day, preferably about 1 mg to about 12 mg per day, and more preferably 5 to 10 mg per day.

The inventive solution comprises an aqueous and solution-stabilizing vehicle that is pharmaceutically acceptable. By a stabilizing solution, it is meant that not more than about 0.2%, preferably not more than about 0.1%, of the cetirizine is degraded into known or unknown impurities under varying temperature and humidity conditions. Impurities are the unwanted chemicals that develop during formulation or upon aging of the formulated active pharmaceutical ingredient. An impurity can be any component present in the intermediate or active ingredient that is not the desired entity. An impurity may be a characterized or unknown chemical entity. The presence of these impurities, even in small amounts, may have an effect on the safety and efficacy of the pharmaceutical product. Organic impurities may arise during the manufacturing process and/or storage of the drug substance. They may be identified or unidentified, volatile or non-volatile, and include starting materials, by-products of the synthesis procedure or degradation products. Although the end products are washed with solvents, there is always the chance of having residual unreacted starting materials. Impurities can also be formed by degradation of the end product during manufacturing of bulk drugs. In general, a pharmaceutical formulation may contain all of the above-mentioned types of organic impurities at levels varying from negligible to significant.

There are several known impurities of cetirizine that are monitored during production of pharmaceutical formulations. 4-Chloro Benzhydryl Piperazine is a starting material in the manufacture of cetirizine active pharmaceutical ingredient. This compound is not a degradation product, and its impurity level in the formulation would depend on the amount that is in starting amount of cetirizine. Cetamide (2-[4-(4-chloro-benzhydryl]-1-piperazinyl)]ethoxy)acetamide is an intermediate in the process of preparing the active pharmaceutical ingredient. Thus, cetamide is a byproduct of the production steps and its impurity level in the formulation would also depend on the amount that is in the originally used cetirizine. Glycerin-cetirizine esters are formed between the cetirizine carboxylic group and the hydroxyl groups of polyhydric alcohols over time. These esters are degradation products and have been previously described for the manufactured cetirizine oral solutions, and in U.S. Pat. No. 6,171,618.

A HPLC method was developed and validated for the determination of cetirizine dihydrochloride as well as its related impurities in the commercial oral solution and the inventive formulation. Test samples of the cetirizine solutions were monitored for active and impurities. The testing was done at room temperature and at accelerated conditions of 30° C. and 40° C. Cetirizine and its impurities were measured by HPLC employing either Agilent (Hewlett-Packard) 1100 HPLC and/or Waters Alliance HPLC System 2695. Chromatograms from the HPLC show the peaks of detectable chemicals in the solution. The method was validated with respect to linearity and range, method accuracy, method precision, method specificity, limit of quantitation and method robustness. The validation method proved the HPLC measurements to be accurate, precise, specific and robust. The measurement of impurities was made by measuring the Relative Retention Time which is a ration of the retention time of the analyte to the retention time of the active, cetirizine.

The guidelines for the International Conference on Harmonization (ICH), require that, for a maximum daily dosage of 10 mg/day for children, any impurity greater than 0.5% in a solution be qualified, any impurity in an amount of greater than 0.2% be identified and any impurity greater than 0.1% be reported. In general, liquid dosage forms are much more susceptible to both degradation and microbiological contamination. In this regard, water content, pH of the solution/suspension and the mutual interactions of ingredients are critical factors. The limit of detection is the minimum concentration (% w/w) at which the analyte can reliably be detected. The limit of quantitation is the minimum concentration (% w/w) at which the analyte can reliably be quantified. Limits of detection and quantitation were determined by comparing measured signals from samples with known low concentrations of analyte to measured signals from blank samples.

The storage stabilizing vehicle of the present invention comprises a thickener component and a carrier component, and may include organoleptic components. Carbomers (Merck Index $12^{th}$ ed., no. 1878) can be used as thickeners in semi-solid pharmaceutical formulations (see Mehta et al., U.S. Pat. No. 6,071,523). Carbomer 934P (Carbopol® 974P) is a suitable thickener or gelling agent. Suitable concentrations from about 0.2 to about 1.0%, and more specifically from about 0.40 to about 0.45%, w/w. Its rheology supports a high yield value (Handbook of Pharmaceutical Excipients Third Ed., A. H. Kibbe (Ed.), Pharmaceutical Press, London, UK, 2000, Pg. 442, 79, 53 ("Handbook of Pharm. Excipients"). Carbomers are slightly acidic and must be neutralized e.g. with sodium hydroxide (as needed to neutralize the carbomer up to about 0.08% in particular formulations) with a preferred pH range being about 6.2 to about 7.3, providing the maximum viscosity plateau. The vehicle carrier component comprises propylene glycol up to about 20%, or from about 3 to about 10%. Glycerin up to about 50% may be present. Additionally, sorbitol, up to 10%, may be added as a vehicle and stabilizer. Purified water comprises the bulk of the carrier component comprising from about 29% to about 64% of the formulation.

The vehicle of the present invention has been described in U.S. Publication No. 2005-0175642 A1, herein incorporated by reference, as a stabilizing composition for a suspension of the piperidine antihistamine, Loratadine.

The solutions of the present invention may also contain Edetate Disodium (EDTA). EDTA is a chelating agent that forms a stable water-soluble complex with alkaline earth and heavy metal ions. It is useful as an antioxidant synergist, sequestering metal ions that might otherwise catalyze autoxidation reactions EDTA may also have synergistic effects as an antimicrobial when used in combination with other preservatives (Handbook of Pharmaceutical Excipients $4^{th}$ Ed.).

Microbiological growth resulting from the growth of bacteria, fungi, and yeast in a humid and warm environment may result in oral liquid products that are unusable for human consumption. Microbial contamination may occur during the shelf life and subsequent consumer-use of a multiple-dose product due to inappropriate use of certain preservatives in the preparations, or because of the semi-permeable nature of primary containers. The solution has antimicrobial activity. Propylparaben (up to about 0.04%) and butylparaben (0.018% to about 0.18%) are suitable. Other antimicrobial excipients may also be used.

Water Activity is a measure of the free or unbound water in a product. Water activity is a critical factor that determines shelf life. Most bacteria will not grow at water activities below 0.80, and most molds cease to grow at water activities below 0.70. By measuring water activity, it is possible to predict which microorganisms will and will not be potential sources of spoilage. Water activity determines the lower limit of available water for microbial growth. In addition to influencing microbial spoilage, water activity can have a major impact their color, taste, and aroma. Water activity was measured using an AwQuick unit (Rotronic Instrument Corporation, Huntington, N.Y.). Initially, the water activity was found to be too high and so sorbitol was introduced to decrease the water level. Water activity measurements are shown in table V.

The organoleptic ingredients improve the taste and appearance and do not negatively affect the solution, stability. The organoleptic agents in the following examples include coloring and flavoring agents, sweeteners and masking agents. The pharmaceutical formulation of the present invention may also contain additional active pharmaceutical ingredients, such as for example, decongestants, analgesics, antitussives and expectorants. Any specific drug within these therapeutic classes is suitable for inclusion in the present invention. Illustrative examples include analgesics such as aspirin, acetaminophen, naproxen, ketoprofen and ibuprofen; decongestants such as pseudoepehedrine or phenylpropanolamine; antitussives such as codeine, hydrocodone, or dextromethorphan; and expectorants such as guaifenesin, including salts thereof.

EXAMPLES

Example 1

The storage stable solution was formulated to contain the following ingredients:

TABLE I

| Cetirizine Storage Stable Formulation | |
|---|---|
| INGREDIENTS | % (w/v) |
| Cetirizine | 0.087 |
| Purified Water | 38.69 |
| Edetate Disodium USP | 0.04 |
| Glycerin | 50 |
| Sorbitol (Crystalline) | 5.0 |
| Propylene Glycol | 5.0 |
| Carbomer 934P (Carbopol ® 974P) | 0.43 |
| Sodium Hydroxide | 0.0116 |
| Sucralose Liquid Concentrate | 0.20 |
| Butylparaben | 0.04 |
| Masking Agent | 0.20 |
| Artificial Grape Flavor | 0.20 |

Example 2

As a comparative example, a cetirizine hydrochloride syrup (5 mg/5 mL) was prepared. The composition of the syrup is as follows:

TABLE II

| Cetirizine Syrup Formulation | |
|---|---|
| INGREDIENTS | % (w/v) |
| Cetirizine | 0.087 |
| Purified Water | q.s. |
| Glycerin | 24.7 |
| Sucrose | 45.1 |
| Propylene Glycol | 12.2 |
| Sodium Acetate (anhydrous) | 0.12 |
| Glacial Acetic Acid | 0.22 |
| Butylparaben | 0.02 |
| Methylparaben | 0.18 |
| Flavoring | 0.15 to 0.25 |

Example 3

Impurities

Table III:

Three exhibit batches of cetirizine spill resistant solution were manufactured with the formulation as given in Example 1. Cetirizine solution sample 1, sample 2, and sample 3 were placed in amber bottles, and placed in an inverted position for a three-month time period for regulatory stability testing. The environmental conditions for the exhibit batches were either room temperature with average relative humidity (RH) (25±2° C.; 60±5% RH), or high temperature with high relative humidity (40±2° C.; 75±5% RH). Total unidentified degradation products of the cetirizine stabilized solution were never above 0.1%. In contrast, after three months of stability testing with the cetirizine syrup as prepared in example 2, glycerin-cetirizine ester was the main degradation product. The total impurities seen in the cetirizine syrup formulations were ten times more than the total impurities seen in the stabilized solution. Additionally, 0.6% of the total impurities measured in the syrup were identified as glycerin-cetirizine ester. Surprisingly, there was no detection of any glycerin-cetirizine ester in the stabilized solution.

TABLE III

| Total Impurities Cetirizine Oral Formulations (HPLC % total active) | | |
|---|---|---|
| | Temperature and Relative Humidity Conditions | |
| Sample | 25 ± 2° C.; 60 ± 5% RH | 40 ± 2° C.; 75 ± 5% RH |
| Cetirizine Solution Sample 1 | 0.07% | 0.06% |
| Cetirizine Solution Sample 2 | 0.09% | 0.08% |
| Cetirizine Solution Sample 3 | 0.09% | 0.07% |
| Cetirizine Syrup | 0.2% | 0.7% (0.6% identified as glycerin-cetirizine ester) |

Table IV:

The impurities of the spill resistant stabilized cetirizine, as described in example 1, was compared to a sample of the commercially available cetirizine syrup. Both samples were placed in amber bottles, and placed in an inverted position for a three-month time period for regulatory stability testing. The environmental conditions for the exhibit batches were either room temperature with average relative humidity (RH) (25±2° C.; 60±5% RH), or high temperature with high relative humidity (40±2° C.; 75±5% RH). Total unidentified degradation products of the cetirizine stabilized solution were never above 0.2% for both room temperature and accelerated conditions. In contrast, after six months of stability testing with the commercial syrup impurity levels of 0.29% at room temperature and 3.51% at high temperature were recorded.

TABLE IV

| Comparison of Impurities in Cetirizine Spill Resistant Solution Vs Cetirizine Commercial Syrup | | | | | |
|---|---|---|---|---|---|
| | | Cetirizine Spill Resistant 5 mg/5 ml | | Commercial Syrup 5 mg/5 ml | |
| | Time | RT | 40° C | RT | 40° C |
| Impurities, individual unidentified | Initial | $LT^2$ 0.05% | LT 0.05% | RRT 1.3: 0.07% | RRT 1.3: 0.07% |

TABLE IV-continued

Comparison of Impurities in Cetirizine Spill Resistant Solution Vs Cetirizine Commercial Syrup

|  |  | Cetirizine Spill Resistant 5 mg/5 ml | | Commercial Syrup 5 mg/5 ml | |
| --- | --- | --- | --- | --- | --- |
|  | Time | RT | 40° C | RT | 40° C |
| Impurities, total | Initial | LT 0.05% | LT 0.05% | 0.07% | 0.07% |
|  | 3 months | 0.08% | 0.15% | 0.13% | 1.83% |
|  | 6 months | 0.06% | 0.05% | 0.29% | 3.51% |

[1]Results shown are the average values from analysis of three lots.
[2]LT = Less Than Example 5

Water Activity

Most bacteria will not grow at water activities below 0.91, and most molds cease to grow at water activities below 0.80. Water activity was measured using an AwQuick unit (Rotronic Instrument Corporation, Huntington, N.Y.). Water activity measurements are shown in table VII.

TABLE V

Water Activities Cetirizine Hydrochloride Spill Resistant

| Lot # | Sorbitol (%) | Water (%) | Butylparaben (%) | Water Activity $A_w$ |
| --- | --- | --- | --- | --- |
| 1 | 0 | ~44% | 0.018 | 0.766 |
| 2 | 0 | ~44% | 0.0144 | 0.771 |
| 3 | 0 | ~44% | 0.009 | 0.766 |
| 4 | 5 | ~39% | 0.018 | 0.723 |
| 5 | 5 | ~39% | 0.0144 | 0.724 |
| 6 | 5 | ~39% | 0.009 | 0.722 |

We claim:

1. A stabilized pharmaceutical formulation comprising cetirizine or a salt thereof, evenly dissolved in a semi-solid spill resistant aqueous vehicle comprising glycerin in an amount of up to about 50% w/w, propylene glycol in an amount from about 3% to about 10% w/w, and carbomer in an amount of about 0.2 to about 1.0% w/w, and having a purity equal to or greater than about 99% by weight-based HPLC assay, residual solvents of less than about 0.5%, and a total impurity of less than about 0.2%.

2. The formulation of claim 1, wherein the total impurity is less than about 0.1%.

3. The formulation of claim 1 having a storage stability of up to 24 months.

4. The formulation of claim 1 having a storage stability of up to 36 months.

5. The formulation of claim 1, further comprising at least one organoleptic agent.

6. The formulation of claim 1, further comprising a decongestant, an analgesic, an antitussive, an expectorant, or any combination of two or more thereof.

7. The formulation of claim 1 having a pH of between about 5.4 and about 8.0.

8. The formulation of claim 3 having a pH of between about 6.2 and about 7.3.

9. A method for treating a human in need of cetirizine comprising the step of administering a therapeutically effective amount of the formulation of claim 1.

10. A method of preventing formation of impurities in a pharmaceutical liquid formulation comprising mixing cetirizine or a salt thereof with a storage stabilizing semi-solid spill resistant aqueous vehicle comprising glycerin in an amount of up to about 50% w/w, propylene glycol in an amount from about 3% to about 10% w/w, and carbomer in an amount of about 0.2 to about 1.0% w/w.

11. A method of providing cetirizine or a salt thereof liquid formulation having an extended product shelf life, that method comprising mixing the cetirizine or salt thereof with a storage stable semi-solid spill resistant aqueous vehicle comprising glycerin in an amount of up to about 50% w/w, propylene glycol in an amount from about 3% to about 10% w/w, and carbomer in an amount of about 0.2 to about 1.0% w/w.

12. The formulation of claim 1, further comprising sorbitol in an amount of up to about 10% w/w.

13. The formulation of claim 1, further comprising water in an amount of from about 29% to about 64% w/w.

14. The formulation of claim 1, wherein the formulation is administered to a patient in a dosage range from about 0.5 to about 15 mg of cetirizine per day.

15. The formulation of claim 1, wherein the formulation comprises cetirizine in an amount of about 0.087% w/w, purified water in an amount of about 38.69% w/w, edetate disodium USP in an amount of about 0.04% w/w, glycerin in an amount of about 50% w/w, sorbitol (crystalline) in an amount of about 5.0% w/w, propylene glycol in an amount of about 5.0% w/w, Carbomer 934P in an amount of about 0.43% w/w sodium hydroxide in an amount of about 0.0116% w/w, sucralose liquid concentrate in an amount of about 0.20% w/w, butylparaben in an amount of about 0.04% w/w, masking agent in an amount of about 0.20% w/w, and artificial grape flavor in an amount of about 0.20% w/w.

* * * * *